United States Patent [19]

Clear et al.

[11] Patent Number: 5,368,584
[45] Date of Patent: Nov. 29, 1994

[54] ABSORBENT ARTICLE WITH DYNAMIC ELASTIC LEG FEATURE COMPRISING ELASTICIZED THIGH PANELS

[75] Inventors: Sandra H. Clear, Maineville; Miguel A. Robles, Glendale; Kimberly A. Dreier, Cincinnati, all of Ohio

[73] Assignee: The Procter & Gamble Company, Cincinnati, Ohio

[21] Appl. No.: 951,608

[22] Filed: Sep. 25, 1992

[51] Int. Cl.$^5$ .................. A61F 13/15; A61F 13/20
[52] U.S. Cl. .................. 604/385.2; 604/358; 604/369; 604/373; 604/385.1; 604/393
[58] Field of Search ............ 604/358, 365, 369, 373, 604/385.1, 385.2, 378, 393, 394, 396

[56] References Cited

U.S. PATENT DOCUMENTS

| | | |
|---|---|---|
| 3,860,003 | 1/1975 | Buell . |
| 4,031,568 | 6/1977 | Huff . |
| 4,300,562 | 11/1981 | Pieniak ............... 604/385.2 |
| 4,355,425 | 10/1982 | Jones et al. . |
| 4,381,781 | 5/1983 | Sciaraffa et al. . |
| 4,515,595 | 5/1985 | Kievit et al. . |
| 4,568,344 | 2/1986 | Suzuki et al. ............... 604/389 |
| 4,661,102 | 4/1987 | Shikata et al. ............... 604/385.2 |
| 4,675,016 | 6/1987 | Meuli et al. . |
| 4,690,681 | 9/1987 | Haunschild et al. . |
| 4,699,622 | 10/1987 | Toussant et al. . |
| 4,743,241 | 5/1988 | Igaue et al. ............... 604/385.2 |
| 4,834,741 | 5/1989 | Sabee . |
| 4,857,067 | 8/1989 | Wood et al. . |
| 4,861,652 | 8/1989 | Lippert et al. . |
| 4,892,528 | 1/1990 | Suzuki et al. . |
| 4,915,767 | 4/1990 | Rajala et al. . |
| 4,938,753 | 7/1990 | Van Gompel et al. . |
| 4,938,757 | 7/1990 | Van Gompel et al. . |
| 4,940,464 | 7/1990 | Van Gompel et al. . |
| 5,055,103 | 10/1991 | Nomura et al. . |
| 5,080,741 | 1/1992 | Nomura et al. . |
| 5,092,861 | 3/1992 | Nomura et al. . |
| 5,143,679 | 9/1992 | Weber et al. . |
| 5,151,092 | 9/1992 | Buell et al. . |
| 5,171,239 | 12/1992 | Igaue et al. ............... 604/385.2 |
| 5,188,627 | 2/1993 | Igaue et al. ............... 604/385.2 |
| 5,234,422 | 8/1993 | Sneller et al. ............... 604/385.2 |

FOREIGN PATENT DOCUMENTS

| | | |
|---|---|---|
| 0323634 | 7/1989 | European Pat. Off. . |
| A059193 | 5/1954 | France ............... 604/394 |
| 58610 | 4/1989 | Japan . |
| 47428 | 4/1992 | Japan . |
| 2244201A | 11/1991 | United Kingdom . |

*Primary Examiner*—Randall L. Green
*Assistant Examiner*—P. Zuttarelli
*Attorney, Agent, or Firm*—Steven W. Miller; E. Kelly Linman; Jacobus C. Rasser

[57] ABSTRACT

Absorbent articles such as disposable diapers, incontinent briefs, diaper holders, training pants and the like, that have an elastic leg feature that provides dynamic fit around the leg of the wearer. Such absorbent articles comprise a liquid previous topsheet; a liquid impervious backsheet; an absorbent core disposed between the topsheet and the backsheet; and an elastic leg feature comprising an elasticized leg cuff and elasticized thigh panels. The elasticized leg cuff is positioned in at least the center leg zone of the elastic leg feature, and comprises one or more elastic members operatively associated in an elastically contractible condition so that the leg cuff is elastically contractible in generally the longitudinal direction. The elasticized thigh panels comprise a stretch laminate that is mechanically stretched so that the elasticized thigh panel is capable of expanding beyond the original planar state of the absorbent article in at least one direction at an angle from the longitudinal direction.

22 Claims, 3 Drawing Sheets

ABSORBENT ARTICLE WITH DYNAMIC ELASTIC LEG FEATURE COMPRISING ELASTICIZED THIGH PANELS

FIELD OF THE INVENTION

The present invention relates to absorbent articles such as diapers, incontinent briefs, diaper holders, and the like, and more particularly, to absorbent articles having elastic leg features providing dynamic fit about the wearer as well as improved comfort characteristics of the absorbent article.

BACKGROUND OF THE INVENTION

Infants and other incontinent individuals wear absorbent articles such as diapers to receive and contain urine and other body exudates. Absorbent articles function both to contain the discharged materials and to isolate these materials from the body of the wearer and from the wearer's garments and bed clothing. Disposable absorbent articles having many different basic designs are known to the art. For example, U.S. Pat. Re. No. 26,152, entitled "Disposable Diaper" issued to Duncan and Baker on Jan. 31, 1967, describes a disposable diaper which has achieved wide acceptance and commercial success.

In order to provide better fit and reduced leakage about the leg of the wearer, absorbent articles have been provided with elastic leg closures. U.S. Pat. No. 3,860,003, entitled "Contractable Side Portions For Disposable Diaper", issued to Kenneth B. Buell on Jan. 14, 1975, describes an elasticized leg cuff disposable diaper which has achieved wide acceptance and commercial success. U.S. Pat. No. 4,743,241 issued to Igaue et al. on May 10, 1988, describes a disposable diaper having a wide pre-stretched elastic leg closure designed to provide lower pressure on the skin to reduce skin marking along the leg of the wearer as well as a high tension for reduced leakage.

However, it has been found that absorbent articles having elastic leg closures still have a tendency to gap or be too tight about the leg during use. As the wearer goes from a standing position to a sitting position, changes occur in the body measurements, particularly in the hips and buttocks, of the wearer thereby causing the diaper to have to change its dimensions to accommodate the changes in the wearer's dimensions. Conventional disposable diapers are made of nonelastic cover materials which are unable to elastically expand to accommodate these wearer changes and have elastic leg features unable to fully elastically expand without placing undue pressure on the wearer's legs. Thus, the elastic leg features and the materials making up the elastic leg features are unable to dynamically elastically expand to accommodate these body dimensions as the wearer moves. As a result, the elastic leg feature tends to gap away from the leg causing an increased likelihood of leakage or undue pressure may be applied to the leg that can cause skin marking.

Thus, it would be advantageous to provide an absorbent article having elastic leg features that provide better fit.

Therefore, it is an object of the present invention to provide an absorbent article having dynamic fit about the leg of the wearer.

It is a further object of the present invention to provide an absorbent article having an elastic leg feature that provides sustained dynamic fit as the wearer moves.

These and other objects of the present invention will be more readily apparent when considered in reference to the following description and when taken in conjunction with the accompanying drawings.

SUMMARY OF THE INVENTION

The present invention provides absorbent articles such as disposable diapers, incontinent briefs, diaper holders, training pants and the like, that have an elastic leg feature that provides dynamic fit around the leg of the wearer. Such absorbent articles comprise a liquid previous topsheet; a liquid impervious backsheet; an absorbent core disposed between the topsheet and the backsheet; and an elastic leg feature comprising an elasticized leg cuff and elasticized thigh panels. The elasticized leg cliff is positioned in at least the center leg zone of the elastic leg feature, and comprises one or more elastic leg members operatively associated in an elastically contractible condition so that the leg cuff is elastically contractible in generally the longitudinal direction. Thus, the elasticized leg cuffs tend to draw and hold the diaper against the leg of wearer, particularly the inner portions of the leg. The elasticized thigh panels comprise a stretch laminate that is mechanically stretched so that the elasticized thigh panel is capable of expanding beyond the original planar state of the absorbent article in at least one direction at an angle from the longitudinal direction. The stretch laminate preferably comprises a zero strain stretch laminate comprising a portion of the topsheet, a portion of the backsheet, and an elastic panel member positioned therebetween.

In an alternative embodiment of the present invention, the elastic panel members of the elasticized thigh panels and the elastic leg member of the elasticized leg cuff comprise the same piece of elastomeric material.

In a further alternative embodiment, the absorbent article additionally comprises elasticized side panels comprising a side panel stretch laminate comprising an elastic side panel member and an elongatable component (typically the topsheet and/or the backsheet), wherein the elastic side panel member, the elastic panel members of the elasticized thigh panels, and the elastic leg member of the elasticized leg cuff are formed of a single piece of elastomeric material. The single piece of elastomeric material is mechanically stretched in the side panels to provide lateral expansion and in the corner leg zones of the elastic leg feature to provide expansion in at least one direction at an angle to the longitudinal direction (preferably in a curvilinear contour) and is at least operatively associated in an elastically contractible condition in the center leg zone, preferably in generally the longitudinal direction.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composed or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, feminine hygiene garments, training pants, and the like.

Figure 1:
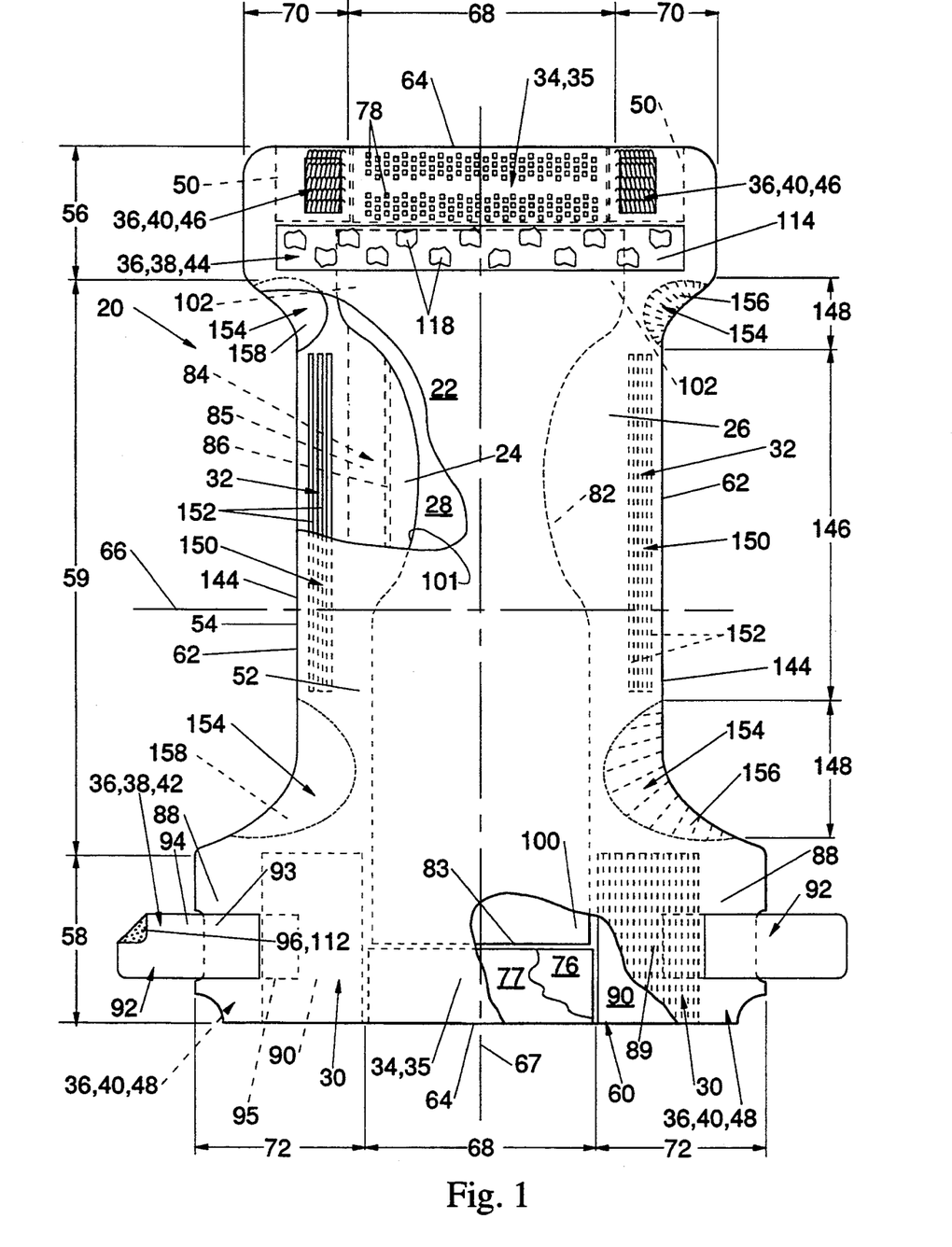
FIG. 1 is a plan view of a disposable diaper embodiment of the present invention having portions cut-away to reveal underlying structure, the outer surface of the diaper facing the viewer.

FIG. 1 is a plan view of the diaper 20 of the present invention in its flat-out, uncontracted state (i.e., with elastic induced contraction pulled out except in the side panels and thigh panels wherein the elastic is left in its relaxed condition) with portions of the structure being cut-away to more clearly show the construction of the diaper 20 and with the portion of the diaper 20 which faces away from the wearer, the outer surface 52, facing the viewer. As shown in FIG. 1, the diaper 20 comprises a containment assembly 22 preferably comprising a liquid previous topsheet 24, a liquid impervious backsheet 26 joined with the topsheet 24, and an absorbent core 28 disposed between the topsheet 24 and the backsheet 26; elasticized side panels 30; an elastic leg feature 32; an elastic waist feature 34; and a closure system comprising a dual tension fastening system generally multiply designated as 36. The dual tension fastening system 36 preferably comprises a primary fastening system 38 and a waist closure system 40. The primary fastening system 38 preferably comprises a pair of securement members 42 and a landing member 44. The waist closure system 40 is shown in FIG. 1 to preferably comprise a pair of first attachment components 46 and a second attachment component 48. The diaper 20 also preferably comprises a positioning patch 50 located subjacent each first attachment component 46. The elastic leg feature 32 preferably comprises (i) an elasticized leg cuff 150 comprising one or more elastic leg members 152 operatively associated in an elastically contractible condition, preferably between the topsheet 24 and the backsheet 26, such that the elasticized leg cuff 150 is elastically contractible in generally the longitudinal direction; and (ii) at least one, preferably a pair of, elasticized thigh panels 154 comprising a stretch laminate 156 comprising one or more elongatable components, typically the topsheet 24 and the backsheet 26, and an elastic panel member 158. As shown in FIG. 1, the stretch laminate 156 has been mechanically stretched so that the elasticized thigh panel 154 is capable of elastically expanding beyond the original planar state of the diaper 20 (the elongatable components) in at least one direction at an angle from the longitudinal direction. (The direction of stretch in the thigh panels and the side panels are denoted by dashed lines.)

The diaper 20 is shown in FIG. 1 to have an outer surface 52 (facing the viewer in FIG. 1), an inner surface 54 opposed to the outer surface 52, a first waist region 56, a second waist region 58 opposed to the first waist region 56, a crotch region 59 positioned between the first waist region and the second waist region, and a periphery 60 which is defined by the outer perimeter or edges of the diaper 20 in which the longitudinal edges are designated 62 and the end edges are designated 64. The inner surface 54 of the diaper 20 comprises that portion of the diaper 20 which is positioned adjacent to the wearer's body during use (i.e., the inner surface 54 generally is formed by at least a portion of the topsheet 24 and other components joined to the topsheet 24). The outer surface 52 comprises that portion of the diaper 20 which is positioned away from the wearer's body (i.e., the outer surface 52 generally is formed by at least a portion of the backsheet 26 and other components joined to the backsheet 26). The first waist region 56 and the second waist region 58 extend, respectively, from the end edges 64 of the periphery 60 to the crotch region 59. The waist regions each comprise a central region 68 and a pair of side panels which typically comprise the outer lateral portions of the waist regions. The side panels positioned in the first waist region 56 are designated 70 while the side panels in the second waist region 58 are designated 72. (In the discussion that follows, unless otherwise noted, the diaper 20 will comprise a pair of side panels in each waist region. While it is not necessary that the pairs of side panels or each side panel be identical, they are preferably mirror images one of the other.) In a preferred embodiment of the present invention, the side panels 72 positioned in the second waist region 58 are elastically extensible, preferably elastically expandable, in the lateral direction (i.e., elasticized side panels 30). (The lateral direction (x direction or width) is defined as the direction parallel to the lateral centerline 66 of the diaper 20; the longitudinal direction (y direction or length) being defined as the direction parallel to the longitudinal centerline 67; and the axial direction (Z direction or thickness) being defined as the direction extending through the thickness of the diaper 20.) FIG. 1 shows a preferred embodiment of the diaper 20 in which the topsheet 24 and the backsheet 26 have length and width dimensions generally larger than those of the absorbent core 28. The topsheet 24 and the backsheet 26 extend beyond the edges of the absorbent core 28 to thereby form the periphery 60 of the diaper 20.

The containment assembly 22 of the diaper 20 is shown in FIG. 1 as comprising the main body (chassis) of the diaper 20. The containment assembly 22 comprises at least an absorbent core 28 and preferably an outer covering layer comprising the topsheet 24 and the backsheet 26. When the absorbent article comprises a separate holder and a liner, the containment assembly 22 generally comprises the holder and the liner (i.e., the containment assembly 22 comprises one or more layers of material to define the holder while the liner comprises an absorbent composite such as a topsheet, a backsheet, and an absorbent core.) For unitary absorbent articles, the containment assembly 22 comprises the main structure of the diaper with other features added to form the composite diaper structure. Thus, the containment assembly 22 for the diaper 20 generally comprises the topsheet 24, the backsheet 26, and the absorbent core 28.

The absorbent core 28 may be any absorbent means which is generally compressible, conformable, non-irritating to the wearer's skin, and capable of absorbing and retaining liquids such as urine and other certain body exudates. As shown in FIG. 1, the absorbent core 28 has a garment surface 100, a body surface 101, side edges 82, and waist edges 83.

The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, cross-linked cellulosic fibers, tissue including tissue wraps and tissue laminates, absorbent foams, absorbent sponges, superabsorbent polymers, absorbent gelling materials, or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the diaper 20. Further, the size and absorbent capacity of the absorbent core 28 may be varied to accommodate wearers ranging from infants through adults.

A preferred embodiment of the diaper 20 has an asymmetric, modified T-shaped, absorbent core 28 having ears 102 in the first waist region 56 but a generally rectangular shape in the second waist region 58. This configuration allows wider elasticized side panels 30 in the second waist region 58. An exemplary absorbent structure for use as the absorbent core 28 of the present invention that has achieved wide acceptance and commercial success is described in U.S. Pat. No. 4,610,678 entitled "High-Density Absorbent Structures" issued to Weisman and Goldman on Sep. 9, 1986. U.S. Pat. No. 4,673,402 entitled "Absorbent Articles With Dual-Layered Cores" issued to Weisman, Houghton, and Gellert on Jun. 16, 1987; and U.S. Pat. No. 4,888,231 entitled "Absorbent Core Having A Dusting Layer" issued to Angstadt on Dec. 19, 1989; also describe absorbent structures that are useful in the present invention. The absorbent core 28 may also comprise the commercially successful absorbent member described in U.S. Pat. No. 4,834,735, entitled "High Density Absorbent Members Having Lower Density and Lower Basis Weight Acquisition Zones", issued to Alemany and Berg on May 30, 1989. The absorbent core may further comprise the dual core system containing an acquisition/distribution core of chemically stiffened fibers positioned over the absorbent storage cores as detailed in co-pending U.S. patent application Ser. No. 07/843,706, "Absorbent Article With Elastic Waist Feature and Enhanced Absorbency", Clear and Alemany, filed on Feb. 28, 1992; and in US. Pat. No. 5,147,345, "High Efficiency Absorbent Articles For Incontinence Management" issued to Young, LaVon and Taylor on Sep. 15, 1992. All of these references are incorporated herein by reference.

The backsheet 26 is positioned adjacent the garment surface 100 of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by Century Adhesives, Inc. of Columbus, Ohio and marketed as Century 5227; and by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola and Tucker on Mar. 4, 1986, and which is incorporated herein by reference. An exemplary attachment means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils).

In a preferred embodiment of the present invention, at least a portion of the backsheet 26 is subjected to mechanical stretching in order to provide both a "zero strain" stretch laminate that forms the elasticized side panels 30 and/or the elasticized thigh panels 154 and, optionally, to prestrain a portion of the backsheet coinciding with the other elastic features. Thus, the backsheet is preferably elongatable, most preferably drawable, but not necessarily elastomeric, so that the backsheet will, upon mechanical stretching, be at least to a degree permanently elongated such that it will not fully return to its original undistorted configuration. In preferred embodiments, the backsheet can be subjected to mechanical stretching without undue rupturing or tearing. Thus, it is preferred that the backsheet have an ultimate elongation to break of at least about 400% to about 700% in the cross-machine direction as measured using a method consistent with ASTM D-638. Thus, preferred polymeric films for use as the backsheet contain a high content of linear low density polyethylene. Particularly preferred materials for the backsheet include blends comprised of about 45–90% linear low density polyethylene and about 10–55% polypropylene. Exemplary films for use as the backsheet of the present invention are manufactured by Tredegar Industries, Inc. of Terre Haute, Ind. under the designation RR8220 blend for blown films and RR5475 blend for cast films. The backsheet 26 is preferably embossed (typically, to a caliper of about 0.127 mm (5.5 mils)) and/or matte finished to provide a more clothlike appearance. Further, the backsheet 26 may permit vapors to escape from the absorbent core 28 (i.e., breathable) while still preventing exudates from passing through the backsheet.

The size of the backsheet 26 is dictated by the size of the absorbent core 28 and the exact diaper design selected. In a preferred embodiment, the backsheet 26 has a modified hourglass shape extending beyond the absorbent core 28 around the entire diaper periphery 60. Preferably, the backsheet 26 is much wider than the absorbent core 28 in the second waist region 58 so that the side panels 72 in the second waist region 58 are generally wider in the lateral direction than the side panels 70 in the first waist region 56.

The topsheet 24 is positioned adjacent the body surface 101 of the absorbent core 28 and is preferably joined thereto and to the backsheet 26 by attachment means (not shown) such as those well known in the art. Suitable attachment means are described with respect to joining the backsheet 26 to the absorbent core 28. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 24 and the backsheet 26 are joined directly to each other in the diaper periphery 60 and are indirectly joined together by directly joining them to the absorbent core 28 by the attachment means (not shown).

The topsheet 24 is compliant, soft feeling, and non-irritating to the wearer's skin. Further, the topsheet 24 is liquid previous permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of a hydrophobic material to better isolate the wearer's skin from liquids contained in the absorbent core 28 (i.e., prevent "rewet").

In a preferred embodiment of the present invention, at least a portion of the topsheet 24 is subjected to mechanical stretching in order to provide a "zero strain" stretch laminate that forms the elasticized side panels 30 and/or the elasticized thigh panels 154. Thus, the topsheet is preferably elongatable, most preferably drawable, but not necessarily elastomeric, so that the topsheet will, upon mechanical stretching, be at least to a degree permanently elongated such that it will not fully return to its original configuration. In preferred embodiments, the topsheet can be subjected to mechanical stretching without undue rupturing or tearing of the topsheet. Thus, it is preferred that the topsheet have a low cross-machine direction (lateral direction) yield strength.

There are a number of manufacturing techniques which may be used to manufacture the topsheet 24. For example, the topsheet may be a nonwoven web of fibers. When the topsheet comprises a nonwoven web, the web may be spunbonded, carded, wet-laid, meltblown, hydroentangled, combinations of the above, or the like. A preferred topsheet is carded and thermally bonded by means well known to those skilled in the fabrics art. A preferred topsheet comprises staple length polypropylene fibers having a denier of about 2.2. As used herein, the term "staple length fibers" refers to those fibers having a length of at least about 15.9 mm (0.625 inches). Preferably, the topsheet has a basis weight from about 18 to about 25 grams per square meter. A suitable topsheet is manufactured by Veratec, Inc., a Division of International Paper Company, of Walpole, Mass. under the designation P-8.

The elastic leg features 32 of the present invention provide improved dynamic fit about the leg. Each elastic leg feature 32 extends laterally outwardly from the side edge 82 of the absorbent core 28 in the crotch region 59 and generally forms at least a portion of the longitudinal edge 62 of the diaper 20, typically the curvilinear side notch portion of the longitudinal edge 62, herein designated as the leg edge 144. Thus, the elastic leg feature 32 comprises that portion of the diaper 20 extending from the side edge 82 of the absorbent core 28 to the leg edge 144 and is intended to be placed about the wearer's leg during use. While the elastic leg feature 32 or any of its constituent elements can comprise a separate element affixed to the containment assembly 22 of the diaper 20, the elastic leg feature 32 will be described with respect to a preferred embodiment in which the elastic leg feature 32 is partially constructed as an extension of other elements of the diaper 20 such as the backsheet 26 or the topsheet 24, preferably both the backsheet 26 and the topsheet 24.

The elastic leg feature 32 has a center leg zone 146 and a pair of corner leg zones 148, one at each end of the center leg zone 146. The center leg zone 146 is that portion of the elastic leg feature 32 designed to fit about the inner segments of the wearer's thighs and is typically the middle rectilinear portion of the leg edge 144. The corner leg zones 148 are contiguous with the center leg zone 146 and extend longitudinally outward from the ends of the center leg zone 146. The corner leg zones 148 are designed to fit about the outer segments of the wearers thigh and typically form the curvilinear end segments of the leg edge 144.

The elastic leg feature 32 comprises an elasticized leg cuff 150 and at least one, preferably a pair of, elasticized thigh panels 154. The elasticized leg cuffs 150 are positioned in at least the center leg zone 146 of the elastic leg feature 32 while the elasticized thigh panels 154 are positioned in the corner leg zones 148. The elasticized leg cuffs 150 are elastically contractible in the longitudinal direction while the elasticized thigh panels 154 are elastically expandable in at one direction at an angle from the longitudinal direction, preferably along a curvilinear contour corresponding to the contour of the leg edge 144.

The elasticized leg cuffs 150 are disposed in at least the center leg zone 146 of the elastic leg feature 32 so that the elasticized leg cuffs 150 tend to draw and hold the diaper against the legs of the wearer. The elasticized leg cuffs 150 are elastically contractible in generally the longitudinal direction. While the elasticized leg cuffs 150 may comprise any of several constructions, including stretch laminates, heat shrinkable elastic leg features, or the like; a preferred elasticized leg cuff construction comprises a portion of the topsheet 24, a portion of the backsheet 26, and one or more elastic leg members 152 operatively associated in an elastically contractible condition with the topsheet 24, the backsheet 26, or both. Such a preferred construction is described in U.S. Pat. No. 3,860,003 entitled "Contractable Side Portions For a Disposable Diaper" issued to Buell on Jan. 14, 1975, which patent is incorporated herein by reference. In addition, a method and apparatus suitable for manufacturing a disposable diaper having elastically contractible leg cuffs are described in U.S. Pat. No. 4,081,301 entitled "Method and Apparatus for Continuously Attaching Discrete, Stretched Elastic Strands to Predetermined Isolated Portions of Disposable Absorbent Articles" which issued to Buell on Mar. 28, 1978 and which patent is incorporated herein by reference.

The elastic leg members 152 are operatively associated with the elasticized leg cuff 150, preferably between the topsheet 24 and the backsheet 26, so that the elastic leg members 152 allow the elasticized leg cuff 150 to be elastically contractible in the longitudinal direction (i.e., longitudinally elastically contractible). The elastic leg member 152 is operatively associated in an elastically contractible condition so that the elastic leg member(s) gathers or contracts the elasticized leg cuff 150. For example, the elastic leg members 152 can be contractibly affixed in the elasticized leg cuff 150 by extending the elastic leg member 152, affixing the elastic leg member 152 to either or both the topsheet 24 and the backsheet 26, and allowing the elastic leg member 152 to assume its relaxed or contracted orientation. Alternatively, the elastic leg member 152 may additionally be operatively associated in an elastically contractible condition and subjected to mechanical stretching to form a pretensioned stretch laminate. Further, the elastic leg member 152 can be operatively associated in an elastically contractible condition in an uncontracted state and then treated to contract such as the materials which contract unidirectionally and become elastic following specific treatment such as heating (heat shrinkable elastomeric materials). Examples of such materials are disclosed in U.S. Pat. No. 3,819,401 issued to Massengale, et al. on Jun. 25, 1974 and in U.S. Pat. No. 3,912,565 issued to Koch, et al. on Oct. 14, 1975. A more detailed description of a manner for using a heat-shrinkable elastomeric member is described in U.S. Pat. No. 4,515,595 issued to Kievit and Osterhage on May 7, 1985; this patent being incorporated herein by reference.

The elastic leg members 152 useful in the present invention may take on a number of different sizes, shapes, configurations, and materials. For example, the elasticized leg cuff 150 may be formed from one or a plurality of elastic leg members; the elastic leg members may have varying widths and lengths; or the elastic leg members may comprise relatively narrow strands of elastomeric material or a larger area patch of elastomeric material. One elastomeric material which has been found to be suitable for use as the elastic leg member is an elastomeric foam such as the crosslinked natural rubber foams or polyurethane foams described hereinafter for use as the elastomeric materials of the elasticized thigh panels or the elasticized side panels. Other suitable elastomeric materials for use as the elastic leg members 152 include "live" synthetic or natural rubber, elastomeric films (including heat-shrinkable elastomeric films), formed elastomeric scrim, or the like. In a preferred embodiment as is shown in FIG. 1, the elastic leg members 152 are elastic strands of natural rubber or LYCRA such as the natural rubber strands marketed by Fulflex Inc. of Middletown, R.I.

The elastic leg feature 32 further comprises an elasticized thigh panel 154 disposed in at least one, preferably each, corner leg zone 148 of the elastic leg feature 32. (As used herein, the term "disposed" is used to mean that an element(s) of the diaper is formed (joined and positioned) in a particular place or position as a unitary structure with other elements of the diaper or as a separate element joined to another element of the diaper.) The elasticized thigh panels 154 provide an elastically expandable feature that provides a more comfortable and contouring fit about the leg of the wearer by initially conformably fitting the diaper 20 to the leg and sustaining this fit throughout the time of wear since the elasticized thigh panels 154 allow portions of the elastic leg feature 32 to elastically expand with the leg and return to their original configuration when the leg contracts. While the diaper 20 of the present invention preferably has the elasticized thigh panels 154 disposed in both of the corner leg zones 148 of the elastic leg feature 32; alternatively, the diaper 20 may be provided with an elasticized thigh panel 154 disposed only in one of the corner leg zones, particularly the corner leg zone positioned adjacent the first waist region 56.

The elasticized thigh panels 154 need to be elastically expandable in at least one direction at an angle to the longitudinal direction to better fit the leg of the wearer by providing expansion in a direction that better follows the leg. Elastically expandable "in at least one direction at angle to the longitudinal direction" means that the panel can expand at least at one point (or at a number of or all points) in a direction other than the longitudinal direction and the lateral direction (1° to 89° from the longitudinal direction). It should be noted, however, that segments of the panel may be elastically expandable in the longitudinal or lateral direction provided that expansion at an angle is provided in some segment. Preferably, the elasticized thigh panels 154 are elastically expandable generally in a curvilinear contour to follow the curvilinear shape of the leg edge 144 in the corner leg zones 148. As used herein, the term elastically expandable "in a curvilinear contour" means that the elastic feature is capable of expanding in different directions along the feature in a manner such that the directions of expansion follow a curved line. Thus, as shown by the dashed lines of stretching shown in FIG. 1, the elasticized thigh panels 154 are capable of elastically expanding along the curved segment of the leg edge 144 in the corner leg zones 146. As discussed hereinafter, the curvilinear expansion is achieved by stretching the laminate at an angle to the leg edge 144. Generally, the stretching is done at a right angle to the tangent line at the particular point on the leg edge to provide the maximum stretch; however, other patterns are possible including radial patterns or other differential stretch patterns.

The elasticized thigh panels 154 comprise a stretch laminate 156 so that the elasticized thigh panels are capable of expanding beyond the original planar state of the diaper 20. The stretch laminate 156 comprises an elastic panel member 158 and an elongatable component typically the topsheet 24, the backsheet 26, or both) that have been mechanically stretched as hereinafter described. This stretch laminate 156 allows for expansion of the elasticized thigh panel 154 well beyond the dimensions of the circumference of the leg opening and beyond the initial dimension of the leg edge 144 (beyond the planar state of the diaper 20 itself). (i.e., The elasticized thigh panels 154 are capable of expanding well beyond the dimension of the circumference of the fixed dimension of the leg closure (even beyond the dimension of the materials initially forming the diaper) so as to follow the wearer's leg movements.)

While the stretch laminate 156 may be constructed in a number of configurations; as shown in FIG. 1, the stretch laminate 156 preferably comprises a portion of the topsheet 24, a portion of the backsheet 26, and an elastic panel member 158 operatively associated with the topsheet 24 or the backsheet 26 or both, most preferably between the topsheet 24 and the backsheet 26. In a preferred embodiment of the present invention, the elastic panel members 158 are operatively associated in an untensioned state so as to form a "zero strain" stretch laminate. As used herein, the term "zero strain" stretch laminate refers to a laminate comprised of at least two plies of material which are secured to one another along at least a portion of their coextensive surfaces while in a substantially untensioned ("zero strain") condition; one of the plies comprising a material which is stretchable and elastomeric (i.e., it will return substantially to its untensioned dimensions after an applied tensile force has been released) and a second ply which is elongatable (but not necessarily elastomeric) so that upon stretching the second ply will be, at least to a degree, permanently elongated so that upon release of the applied tensile forces, it will not fully return to its original undeformed configuration. The resulting "zero strain" stretch laminate is thereby rendered elastically expandable, at least up to the point of initial stretching, in the direction of initial stretching by mechanically stretching the laminate. Examples of such "zero strain" stretch laminates are disclosed in U.S. Pat. No. 2,075,189 issued to Galligan, et al. on Mar. 30, 1937; U.S. Pat. No. 3,025,199 issued to Harwood on Mar. 13, 1962; U.S. Pat. No. 4,107,364 issued to Sisson on Aug. 15, 1978; U.S. Pat. No. 4,209,563 issued to Sisson on Jun. 24, 1980; and U.S. Pat. No. 4,834,741 issued to Sabee on May 30, 1989. Each of these patents are incorporated herein by reference. Alternatively, the elastic panel member can be operatively associated in a tensioned condition and the resultant laminate then subjected to mechanical stretching to form a pretensioned stretch laminate. For example, the elastic panel member may be operatively associated with the elongatable component in an elastically contractible condition so that the elastic panel member gathers or contracts the laminate. (A more detailed description of a manner in which elastomeric materials may be secured in an elastically contractible condition can be found in the above referenced U.S. Pat. Nos. 3,860,003 and 4,081,301; both patents being incorporated herein by reference.) While either of the elasticized thigh panels 154 of each elastic leg feature 32 may comprise a pretensioned stretch laminate or a zero strain stretch laminate (e.g., the elasticized thigh panel adjacent the first waist region 56 may be a zero strain stretch laminate while the elasticized thigh panel adjacent the back waist region 58 may be a pretensioned stretch laminate, or vice verse); in a preferred embodiment, both elasticized thigh panels 154 of the elastic leg feature 32 comprise the same type of stretch laminate, most preferably each comprise a zero strain stretch laminate.

At least a portion of the stretch laminate 156 containing the elastic panel member 158 is subjected to mechanical stretching sufficient to permanently elongate the elongatable components (preferably the topsheet 24 and the backsheet 26) of the stretch laminate 156. The stretch laminate 156 is then allowed to return to its substantially untensioned condition. Particularly preferred methods and apparatus used for making stretch laminates out of an elongatable component(s) (the topsheet and the backsheet) and an elastomeric member positioned between the same, use meshing corrugated rolls to mechanically stretch the components. A discussion of suitable apparatus and methods for mechanically stretching portions of a diaper is contained in U.S. Pat. No. 4,107,364 issued to Sisson on Aug. 15, 1978 and U.S. Pat. No. 4,834,741 issued to Sabee on May 30, 1989. Particularly preferred apparatus and methods are disclosed in U.S. Pat. No. 5,143,679, "Method For Sequentially Stretching Zero Strain Stretch Laminate Web To Impart Elasticity Thereto Without Rupturing The Web" issued to Weber and Richardson on Sep. 1, 1992; and in co-pending, commonly assigned, U.S. patent application Ser. No. 07/662,536 entitled "Improved Method And Apparatus For Incrementally Stretching A Zero Strain Stretch Laminate Web To Impart Elasticity Thereto"; P&G Case 4339; filed by Gerald M. Weber et al. on Feb. 28, 1991; and U.S. patent application Ser. No. 07/662,537 entitled "Improved Method And Apparatus For Incrementally Stretching Zero Strain Stretch Laminate Web In A Non-Uniform Manner To Impart A Varying Degree of Elasticity Thereto"; P&G Case 4340; filed by Kenneth B. Buell et al. on Feb. 28, 1991; each of the above references being incorporated herein by reference. In the preferred method for forming the elasticized thigh panels 154 constructed using the "zero strain" stretch laminate technology herein disclosed, the meshing teeth on the pairs of corrugated rolls employed to incrementally mechanically stretch the "zero strain" laminate of the elasticized thigh panel 154 are arrayed in the desired configuration to produce expansion in a direction at an angle from the longitudinal direction. In particular, the meshing teeth are preferably arranged in a desired curvilinear configuration to provide expansion along the desired curvilinear contour, most preferably to be perpendicular to the tangent of the point along the leg edge 144 to provide the maximum stretch.

The elastic panel members 158 may take on a number of different sizes, shapes, configurations and materials. One elastomeric material which has been found to be especially suitable for use as the elastic panel member 158 (especially for "zero strain" stretch laminates) is an elastomeric foam having an elongation to break of at least about 400% and an extension force of about 200 grams per inch of sample width at 50% extension of its unstrained length. Exemplary elastomeric foams which have been found suitable for use as an elastic panel member 158 include: (a) crosslinked natural rubber foams preferably having a caliper of approximately 50 mils and a density of 13.3 pounds per cubic foot (0.214 g/cm$^3$), such as is available from Fulflex Inc. of Middletown, R.I.; or as available from Ludlow Composites Corporation of Fremont, Ohio and marketed under the tradename Baby Foam; or (b) polyurethane foams having a caliper of approximately 80 mils and a density of approximately 2.06 pounds per cubic foot (0.033 g/cm$^3$) such as is available from Bridgestone of Yokohama, Japan and marketed under the tradename Bridgestone SG polyurethane foam; or as available from General Foam of Paramus, N.J. and marketed under the designation of Polyurethane Foam No. 40310. Other suitable elastomeric materials for use as the elastic panel members 158 include "live" synthetic or natural rubber, other synthetic or natural rubber foams, elastomeric films (including heat shrinkable elastomeric films), elastomeric scrim, elastomeric woven or nonwoven webs, elastomeric composites such as el astomeric nonwoven laminates, or the like.

As shown in FIG. 1, the elastic panel members 158 each comprises a patch of elastomeric material (elastomeric patch). The length and width of the elastic panel members 158 are dictated by the diaper's functional design. In the particular embodiment shown in FIG. 1, the elastic panel members 158 have a crescent moon shape. It has been found that this shape is desirable from a product performance, process, and aesthetics standpoint. However, many other shapes are possible in the design of the elastic panel members 158.

Based upon the materials used and the manner of constructing the elasticized thigh panels 154, the extension forces at the designed "in-use" extensions of the elasticized thigh panels are preferably low to provide extensibility with reduced pressure on the skin of the wearer. The extension forces of the elasticized thigh panels are preferably less than or equal to about 400 grams$_f$ at extensions of between about 25 mm (1 inch) and about 50 mm (2 inches), preferably less than or equal to about 350 grams$_f$, more preferably less than or equal to about 300 grams$_f$, at extensions of between about 25 mm (1 inch) and about 50 mm (2 inches). These force/extension characteristics of the elasticized thigh panels represent the primary design criteria. The elasticized thigh panels of the present invention are more preferably designed to have force/extension characteristics such that the extension forces of the elasticized thigh panels are less than or equal to about 400 grams$_f$, preferably less than or equal to about 350 grams$_f$, and more preferably less than or equal to about 300 grams$_f$, at extensions of between about 25 mm (1 inch) and about 76 mm (3 inches). While these secondary design criteria for the elasticized thigh panels appear to be broader than the primary design criteria since the extension ranges are broader, it will be recognized by those of skill in the art that these design criteria are, in fact, narrower since the elasticized thigh panels must undergo an additional 26 mm (1 inch) (from 50 mm to 76 mm) of stretch while maintaining a value for its extension forces less than or equal to the designed target extension force. (Thus, for the additional incremental extension of between 50 mm (2 inches) and about 76 mm (3 inches) the extension forces are less than or equal to about 400 grams$_f$, preferably 350 grams$_f$, more preferably 300 grams$_f$.

In a preferred embodiment of the present invention, the diaper 20 further comprises elasticized barrier cuffs 84 for providing improved containment of liquids and other body exudates. Each elasticized barrier cuff 84 may comprise several different embodiments for reducing the leakage of body exudates in the legs. (The barrier cuffs can be and are sometimes also referred to as stand-up cuffs, containment flaps, leakage control shields, etc.). U.S. Pat. No. 4,909,803 entitled "Disposable Absorbent Article Having Elasticized Flaps" issued to Aziz and Blaney on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including an elasticized leg cuff (gasketing cuff) and an elasticized barrier cuff. U.S. Pat. 4,704,115 entitled "Disposable Waist Containment Garment" issued to Buell on Nov. 3, 1987, discloses a disposable diaper or incontinent garment having side-edge-leakage-guard gutters configured to contain free liquids within the garment. Each of these patents are incorporated herein by reference. While each elasticized barrier cuff 84 may be configured so as to be similar to any of the elasticized flaps, barrier cuffs, gutters, or stand-up flaps described above, each elasticized barrier cuff 84 preferably comprises a barrier flap 85 and one or more spacing elastic members 86 such as constructions described in the above-referenced U.S. Pat. Nos. 4,909,803 and 4,695,278.

The diaper 20 preferably further comprises an elastic waist feature 34 that provides improved fit and containment about the waist of the wearer. The elastic waist feature 34 at least extends longitudinally outwardly from at least one of the waist edges 83 of the absorbent core 28 in at least the central region 68 and generally forms at least a portion of the end edge 64 of the diaper 20. Thus, the elastic waist feature 34 comprises that portion of the diaper 20 at least extending from the waist edge 83 of the absorbent core 28 to the end edge 64 of the diaper 20 and is intended to be placed adjacent the wearer's waist. Disposable diapers are generally constructed so as to have two elastic waist features, one positioned in the first waist region 56 and one positioned in the second waist region 58. While a disposable diaper of the present invention can be constructed with a single elastic waist feature encircling the wearer, the discussion regarding the elastic waist feature will focus on diapers having a pair of elastic waist features, at least one, and preferably both, being constructed according to the technologies described in U.S. patent application Ser. No. 07/750,775, "Absorbent Article With Dynamic Elastic Waist Feature Having A Predisposed Resilient Flexural Hinge", Buell, Clear & Falcone, filed on Aug. 22, 1991, allowed; the specification and drawings of which are incorporated herein by reference. Further, while the elastic waist feature 34 or any of its constituent elements can comprise a separate element affixed to the containment assembly 22 of the diaper 20, the elastic waist feature 34 will be described with respect to a preferred embodiment in which the elastic waist feature 34 is constructed as an extension of other elements of the diaper such as the backsheet 26 or the topsheet 24, preferably both the backsheet 26 and the topsheet 24.

The elasticized waistband 35 provides a member that maintains a defined area coverage, contacts the wearer's waist, and is elastically extensible in at least the lateral direction so as to dynamically fit against the waist of the wearer and to dynamically conform to the waist of the wearer so as to provide improved fit. The elasticized waistband 35 preferably comprises a portion of the topsheet 24, a portion of the backsheet 26 that has preferably been mechanically stretched prior to incorporation into the elasticized waistband 35 (mechanically prestrained), and a bi-laminate material comprising an elastomeric member 76 positioned between the topsheet 24 and the backsheet 26 and a resilient member 77 positioned between the backsheet 26 and the elastomeric member 76. The elasticized waistband 35 is also provided with regions of securement 78 wherein the backsheet 26 and the topsheet 24 are joined to the bi-laminate material of the elastomeric member 76 and the resilient member 77. Since the topsheet 24 and the backsheet 26 are gathered when the bi-laminate material is in its relaxed condition, regions of differential securement are provided which form pleats.

In a preferred embodiment, the diaper also comprises elasticized side panels 30 disposed in the second waist region 58. The elasticized side panels 30 provide an elastically extensible, preferably elastically expandable, feature that provides a more comfortable and contouring fit by initially conformably fitting the diaper to the wearer and sustaining this fit throughout the time of wear well past when the diaper has been loaded with exudates since the elasticized side panels 30 allow the sides of the diaper to expand and contract. The elasticized side panels 30 further provide more effective application of the diaper 20 since even if the diaperer pulls one elasticized side panel 30 farther than the other during application (asymmetrically), the diaper 20 will "self-adjust" during wear. While the diaper 20 of the present invention preferably has the elasticized side panels 30 disposed in the second waist region 58; alternatively, the diaper 20 may be provided with elasticized side panels 30 disposed in the first waist region 56 or in both the first waist region 56 and the second waist region 58. While the elasticized side panels 30 may be constructed in a number of configurations, examples of diapers with elasticized side panels positioned in the ears (ear flaps) of the diaper are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; and the hereinbefore referenced U.S. patent application Ser. No. 07/750,775 of Buell, Clear & Falcone, filed on Aug. 22, 1991 allowed; each of which are incorporated herein by reference. The preferred elasticized side panels preferably comprise a side panel stretch laminate 89 comprising an elongatable component(s) (typically a portion of the topsheet 24 and a portion of the backsheet 26) and an elastic side panel member 90 positioned therebetween that is mechanically stretched. The side panel stretch laminate 89 preferably comprises a zero strain stretch laminate formed using the method and apparatus as previously described herein and in U.S. Pat. No. 5,143,679.

The diaper 20 is also preferably provided with a closure system (tensioning means) for dynamically creating/maintaining lateral tension through the elasticized waistband 35. The lateral tension dynamically created and maintained by the closure system "activates" the stretch of the elasticized waistband 35 thereby allowing it to more dynamically expand and contract with the motions of the wearer. Gapping of the elasticized waistband is also reduced by the activated stretch since it is held in tension to snugly fit against the wearer's waist both when the diaper is initially fitted to the wearer and during use. Further, rollover of the elasticized waistband is reduced by the tension created/maintained by the closure system. Thus, the closure system improves the fit and containment characteristics of the diaper.

While the closure system may take on a number of configurations such as adhesive tape tabs, mechanical closure tape tabs, fixed position fasteners, or any other means for tensioning the elasticized waistband as are known in the art; as shown in FIG. 1, the closure system preferably comprises a waist closure system 40 comprising at least one, typically a pair of, first attachment components 46 and at least one second attachment component 48. More preferably, the closure system additionally comprises a primary fastening system 38 such that the diaper 20 has a dual tension fastening system 36. Preferred embodiments of a diaper having a dual tension fastening system are described in commonly assigned, co-pending, U.S. patent application Ser. No. 07/714,475, P&G Case 4412, Weil et al., "Absorbent Article With Fastening System Providing Dynamic Elasticized Waistband Fit", filed Jun. 13, 1991; and the above referenced U.S. patent application Ser. No. 07/750,775 of Buell, et al. filed on Aug. 22, 1991, allowed; the specification and drawings of each being incorporated herein by reference.

The diaper 20 additionally comprises a positioning patch 50 located subjacent the first attachment component 46. The positioning patch 50 raises the first attachment component 46 in the Z direction (thickness) to allow the first attachment component 46 to come in better contact with the second attachment component 48 and allow the waist closure system to more easily be closed (with less effort). Thus, the waist closure system 40 is more effectively passively activated. The positioning patch 50 also provides a zone of increased flexural stiffness that reduces the tendency of the flexible ear flaps to fold over onto the first attachment component(s) 46 thereby occluding the hooks from being secured during diaper application. Thus, the positioning patch 50 can comprise any element that provides a Z direction build up to the first attachment components 46. As shown in FIG. 1, the positioning patches 50 each comprise a rectangular-shaped piece of material positioned subjacent the first attachment component 46. While the positioning patches 50 may be positioned directly subjacent the first attachment components 46, the positioning patches 50 are preferably positioned between the topsheet 24 and the backsheet 26. In order to provide a flexurally stiff circumference about the waist of the wearer, the lateral edges of the positioning patches can be abutted to or slightly overlapped with the side edges of the elastic waistband member 76. The positioning patches 50 preferably comprise a patch of elastomeric foam. More preferably, during manufacture of the diaper, the positioning patches 50 are formed of the same material as the elastic side panel member 90 with the elastic side panel member 90 of one diaper and the positioning patch 50 of the adjacent diaper being formed from the same segment of material that is then cut after the diaper is completed. Thus, the positioning patch 50 extends from the end edge 64 of the diaper 20 inward toward the center of the diaper 20.

The diaper 20 is preferably applied to a wearer by positioning one of the waist regions, preferably the second waist region 58, under the wearer's back and drawing the remainder of the diaper between the wearer's legs so that the other waist region, preferably the first waist region 56, is positioned across the front of the wearer. The tab portions 94 of the tape tabs 92 are then released from the release portion 95. The diaperer then wraps the elasticized side panel 30 around the wearer, while still grasping the tab portion 94. The elasticized side panel 30 will typically be extended and tensioned during this operation so as to conform to the size and shape of the wearer. The first fastening component 112, the adhesive attachment layer 96, is secured to the second fastening component 114 of the landing member 44 to effect a side closure forming the initial fit dimension of the leg closure. In the preferred embodiment of the present invention, when the side closure is formed, the waist closure is also "automatically" formed, i.e., the waist closure is passively activated such that the elasticized waistband 35 is pretensioned so as to provide fit and containment benefits.

Figure 2:
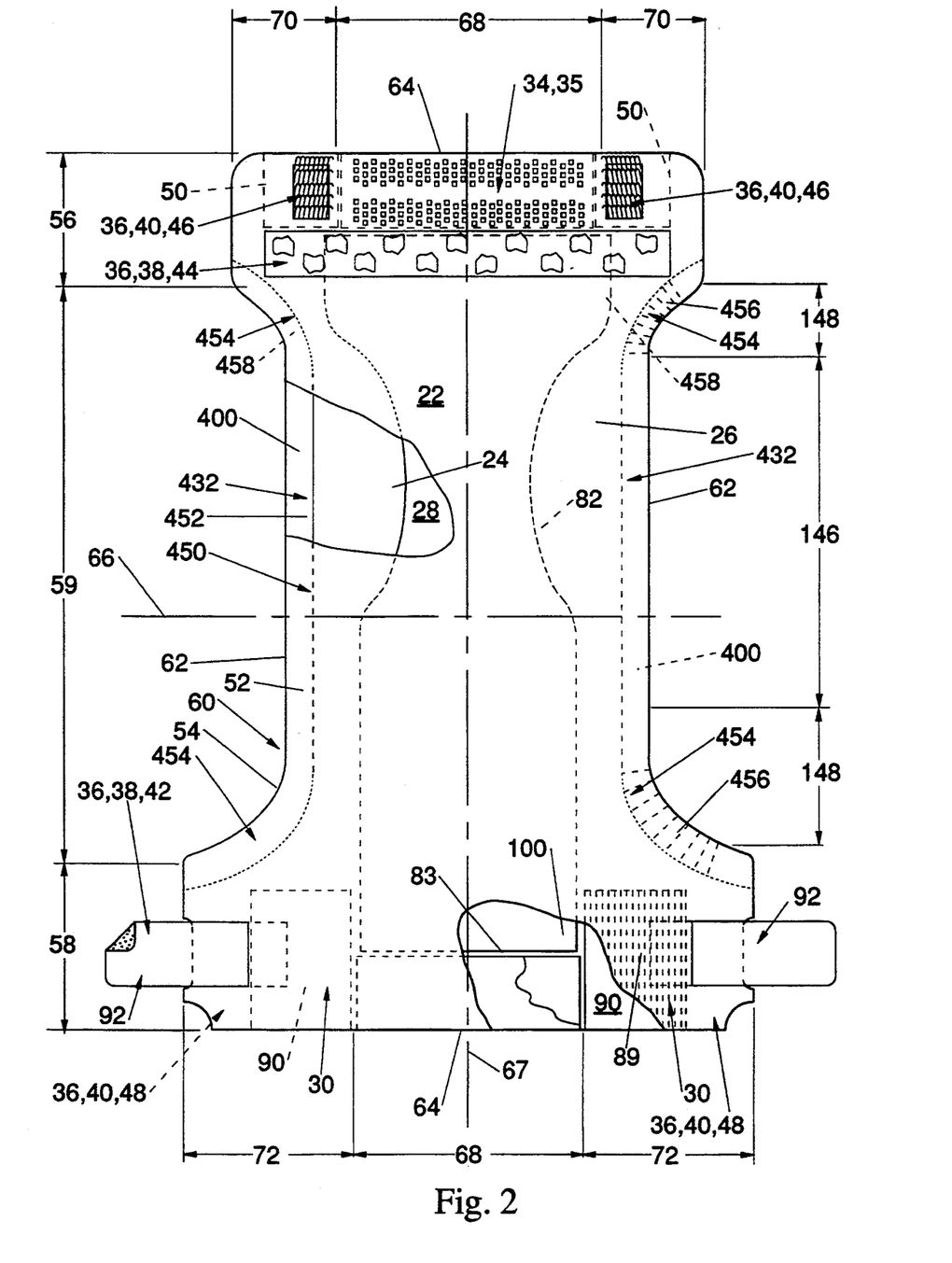
FIG. 2 is a plan view of an alternative disposable diaper embodiment of the present invention wherein the elastic leg closure comprises a single elastomeric member.

FIG. 2 shows an alternative embodiment of the present invention. The elastic leg feature of this embodiment is designated 432. The elastic leg member 452 of the elasticized leg cuff 450, and the elastic panel members 458 of the elasticized thigh panels 454 consist of the same piece of elastomeric material 400. The single piece of elastomeric material 400 preferably extends longitudinally from the corner leg zone 148 adjacent the first waist region 56 to the other corner leg zone 148 adjacent the second waist region 58. The portion of the single piece of elastomeric material positioned in the center leg zone 146 is operatively associated in an elastically contractible condition with either or both of the topsheet 24 and the backsheet 26. The portions of the single piece of elastomeric material positioned in the corner leg zones 148 are preferably joined in a relaxed condition so that these portions, when mechanically stretched, form zero strain stretch laminates forming the elasticized thigh panels 454. Alternatively, the portion of the single piece of elastomeric material positioned in the center leg zone 146 may be mechanically stretched such that the elasticized leg cuff 450 is a pretensioned stretch laminate or it may be operatively associated in a relaxed condition and mechanically stretched to form a zero strain stretch laminate.

Figure 3:
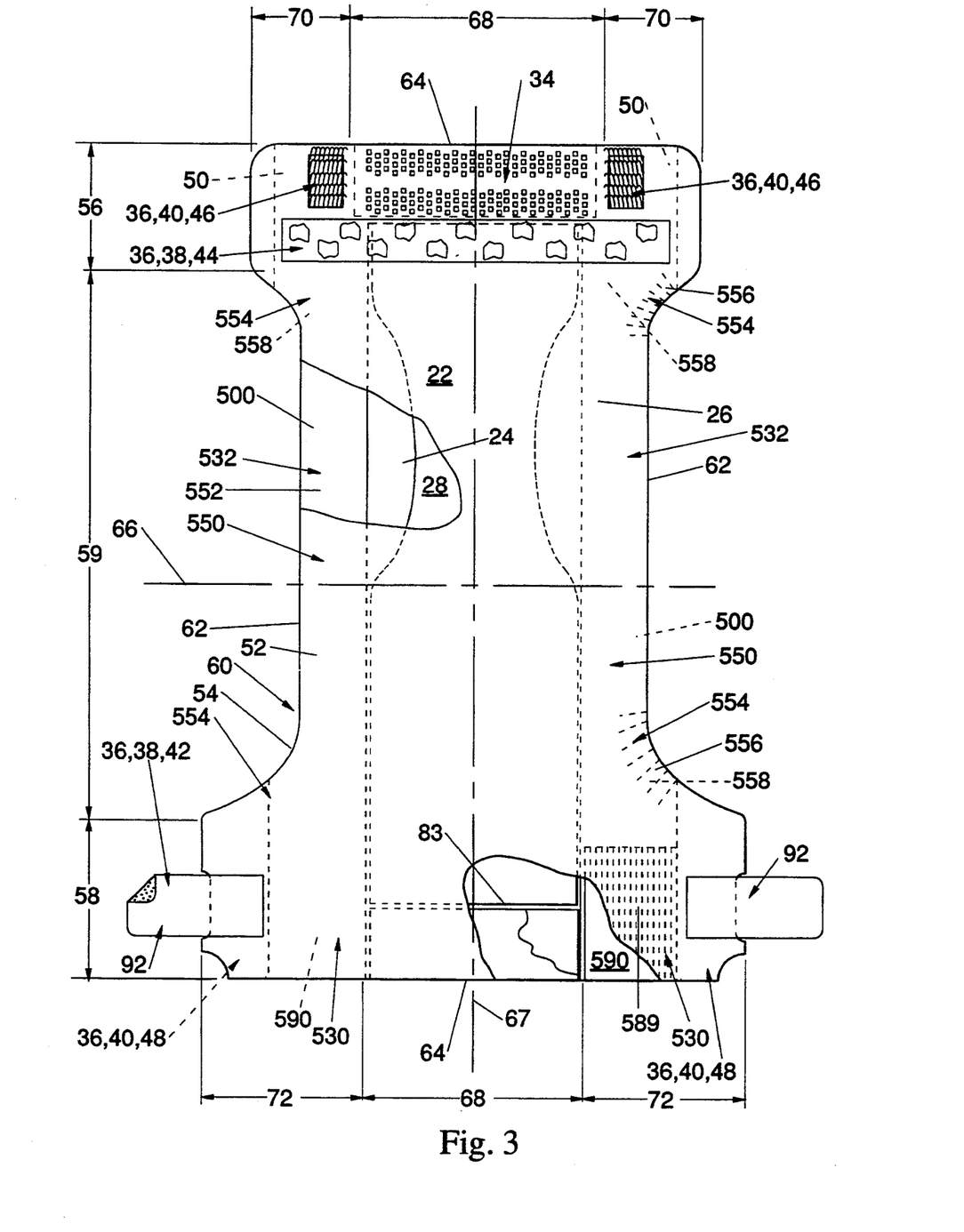
FIG. 3 is a plan view of a further alternative disposable diaper embodiment of the present invention wherein the elastic leg closure and side panels comprise a single elastomeric member.

FIG. 3 shows a further alternative embodiment of the present invention. The elastic leg feature of this embodiment is designated 532. The elastic leg member 552 of the elasticized leg cuff 550, the elastic panel members 558 of the elasticized thigh panels 554, and the elastic side panel member 590 of the elasticized side panel 530 consist of the same piece of elastomeric material 500. The single piece of elastomeric material 500 preferably extends longitudinally from the end edge 64 in the first waist region 56 to the other end edge 64 in the second waist region 58. The portion of the single piece of elastomeric material positioned in the center leg zone 146 is preferably operatively associated in an elastically contractible condition with either or both of the topsheet 24 and the backsheet 26. The portions of the single piece of elastomeric material positioned in the corner leg zones 148 and in the side panel 72 in the second waist region 58 (and in the side panel 70 in the first waist region 56) are preferably joined in a relaxed condition so that the stretch laminates forming the elasticized thigh panels 554 and the elasticized side panels 530, when mechanically stretched, form zero strain stretch laminates. The portion of the single piece of elastomeric material positioned in the first waist region 56 forms the positioning patch 50, although this portion may be eliminated in an alternative embodiment not shown in drawings.

Extention Force Test

The extension force test for the elasticized thigh panels 154 uses an INSTRON Model 4502 as available from Instron Corporation of Canton, Mass. The INSTRON is set for a crosshead speed of 500 mm/min, a chart speed of 500 mm/min, and with full scale at 500 grams$_f$. The INSTRON will be allowed to travel the desired, claimed, or full elastic extension of the thigh panel. (If the full extension of the thigh panel is less than the upper limit claimed, then the test is stopped at this extension since the extension forces at nonextensible areas should not be taken into account; i.e., the designed in-use extension limit has been reached.)

The sample to be tested is taken from the elasticized thigh panel 154. The sample is preferably 25 mm (1 inch) by about 25 mm to about 50 mm so that a sample of 25 mm (1 inch) in the direction of stretch is tested. If an elasticized thigh panel sample of this size cannot be obtained, the test may be carried out using a modified size sample although this is not a preferred situation. The ends of the sample are clamped using standard 1 inch (25 mm) clamps with 1 inch (25 mm) between the clamps. (No zones or areas of the sample should be nonextensible excluding bond sites).

Each sample is run through a travel cycle to the desired, claimed, or full extension of the elasticized thigh panel sample. (The sample may be allowed to contract to also measure contractive force.) A graph of extension force (grams$_f$) versus extension (mm) will be generated. A total of ten samples are run. The extension force at a given extension is the average of the values for the 10 samples.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article having a first waist region, a second waist region, a crotch region between said first waist region and said second waist region, a longitudinal centerline, a longitudinal direction defined as the direction parallel to said longitudinal centerline, a lateral centerline, and a lateral direction defined as the direction parallel to the lateral centerline, longitudinal edges having a curvilinear leg edge, and end edges, the absorbent article comprising:
   a liquid previous topsheet;
   a liquid impervious backsheet joined with said topsheet; an absorbent core having side edges disposed between said topsheet and said backsheet; and
   an elastic leg feature extending laterally outwardly from each of said side edges of said absorbent core in said crotch region, each said elastic leg feature having a center leg zone and a pair of corner leg zones, one at each end of said center leg zone, each said elastic leg feature comprising:
      (i) an elasticized leg cuff positioned in at least said center leg zone, said elasticized leg cuff comprising one or more elastic leg members operatively joined with the absorbent article in an elastically contractible condition such that said elasticized leg cuff is elastically contractible in generally the longitudinal direction; and (ii) an elasticized thigh panel positioned in at least one of said corner leg zones, each said elasticized thigh panel comprising a stretch laminate comprising an elastic panel member and an elongatable component having an original planar state, said stretch laminate being mechanically stretched so that said elasticized thigh panel can expand beyond the original planar state of said elongatable component in at least one direction at an angle from the longitudinal and the lateral direction.

2. The absorbent article of claim 1 wherein said elasticized thigh panel comprises a zero strain stretch laminate.

3. The absorbent article of claim 1 wherein said elasticized thigh panel comprises a pretensioned stretch laminate.

4. The absorbent article of claim 2 or 3 wherein said stretch laminate is elastically expandable in a curvilinear contour along said leg edge.

5. The absorbent article of claim I wherein said elasticized thigh panel is positioned in said corner leg zone adjacent said first waist region.

6. A disposable absorbent article having a first waist region, a second waist region, a crotch region between said first waist region and said second waist region, a longitudinal centerline, a longitudinal direction defined as the direction parallel to said longitudinal centerline, a lateral centerline, a lateral direction defined as the direction parallel to said lateral centerline, longitudinal edges having a curvilinear leg edge, and end edges, the absorbent article comprising:
 a liquid previous topsheet;
 a liquid impervious backsheet joined with said topsheet;
 an absorbent core having side edges and disposed between said topsheet and said backsheet; and
 an elastic leg feature extending laterally outwardly from each of said side edges of said absorbent core in said crotch region, each said leg feature having a center leg zone and a pair of corner leg zones, one at each end of said center leg zone, each said elastic leg feature comprising:
  (i) an elasticized leg cuff positioned in at least said center leg zone, said elasticized leg cuff comprising one or more elastic leg members operatively joined with the absorbent article in an elastically contractible condition such that elasticized leg cuff is elastically contractible in generally the longitudinal direction; and
  (ii) an elasticized thigh panel positioned in each said corner leg zone, each said elasticized thigh panel comprising a stretch laminate comprising a portion of said topsheet having an original planar state, a portion of said backsheet having an original planar state, and an elastic panel member positioned therebetween, said stretch laminate being mechanically stretched so that said elasticized thigh panel can expand beyond the original planar state of said topsheet and said backsheet in at least one direction at an angle from the longitudinal direction and the lateral direction.

7. The absorbent article of claim 6 wherein one of said elasticized thigh panels comprises a zero strain stretch laminate.

8. The absorbent article of claim 7 wherein each of said elasticized thigh panels comprises a zero strain stretch laminate.

9. The absorbent article of claim 8 wherein said elastic panel member comprises an elastomeric foam.

10. The absorbent article of claim 9 wherein said stretch laminate is elastically expandable in a curvilinear contour along said leg edge.

11. The absorbent article of claim 10 wherein each said elastic panel member has a crescent moon shape.

12. The absorbent article of claim 11 wherein said elasticized leg cuff comprises a portion of said topsheet, a portion of said backsheet, and a plurality of elastic leg members each comprising a strand of elastomeric material.

13. The absorbent article of claim 6 or 9 wherein said elastic panel members and said elastic leg member of each said elastic leg feature comprise a single piece of elastomeric material.

14. The absorbent article of claim 13 wherein said elasticized leg cuff comprises a pretensioned stretch laminate.

15. The absorbent article of claim 6 wherein said elasticized thigh panels have an extension force of less than or equal to about 400 grams$_f$ at extensions of between about 25 mm and about 50 mm.

16. A disposable absorbent article having a first waist region, a second waist region, a crotch region between said first waist region and said second waist region, a longitudinal centerline, a longitudinal direction defined as the direction parallel to said longitudinal centerline, a lateral centerline, a lateral direction defined as the direction parallel to said lateral centerline, longitudinal edges having a curvilinear leg edge, and end edges, the absorbent article comprising:
 a liquid previous topsheet;
 a liquid impervious backsheet joined with said topsheet;
 an absorbent core having side edges and disposed between said topsheet and said backsheet;
 elasticized side panels disposed in said second waist region, each of said elasticized side panels being elastically extensible in the lateral direction; and
 an elastic leg feature extending laterally outwardly from each of said side edges of said absorbent core in said crotch region, each said elastic leg feature having a center leg zone and a pair of corner leg zones, one at each end of said center leg zone, each said elastic leg feature comprising:
  (i) an elasticized leg cuff positioned at least in said center leg zone, said elasticized leg cuff comprising one or more elastic leg members operatively joined with the absorbent article in an elastically contractible condition such that said elasticized leg cuff is elastically contractible in generally the longitudinal direction; and
  (ii) an elasticized thigh panel positioned in each of said corner leg zones, each said elasticized thigh panel comprising a stretch laminate comprising a portion of said topsheet having an original planar state, a portion of said backsheet having an original planar state, and an elastic panel member positioned therebetween, said stretch laminate being mechanically stretched so that said elasticized thigh panel can expand beyond the original planar state of said topsheet and said backsheet in at least one direction at an angle from the longitudinal direction and the lateral direction.

17. The absorbent article of claim 16 wherein said elasticized side panels each comprise a side panel stretch laminate comprising a portion of said topsheet, a portion of said backsheet, and an elastic side panel member positioned therebetween, wherein said side panel stretch laminate is mechanically stretched.

18. The absorbent article of claim 17 wherein said side panel stretch laminate is a zero strain stretch laminate.

19. The absorbent article of claim 18 wherein said stretch laminate of each said elasticized thigh panel comprises a zero strain stretch laminate.

20. The absorbent article of claim 19 wherein said elastic leg member, said said elastic side panel members, and said elastic side panel member comprise a single piece of elastomeric material.

21. The absorbent article of claim 20 wherein said elastomeric material is an elastomeric foam.

22. The absorbent articleof claim 16 or 20 wherein said stretch laminate of each said elasticized thigh panel is elastically expandable in a curvilinear contour along said leg edge.

* * * * *

UNITED STATES PATENT AND TRADEMARK OFFICE
CERTIFICATE OF CORRECTION

PATENT NO. : 5,368,584

DATED : November 29, 1994

INVENTOR(S) : Sandra H. Clear, et al.

It is certified that error appears in the above-identified patent and that said Letters Patent is hereby corrected as shown below:

Cover Page, Abstract, Line 5, "previous" should read --pervious--.

Column 2, Line 14, "previous" should read --pervious--.

Column 2, Line 18, "leg cliff" should read --leg cuff--.

Column 3, Line 21, "composed" should read -- composted--.

Column 3, Line 48, "previous" should read --pervious--.

Column 7, Line 50, "previous" should read --pervious--.

Column 8, Line 55, "wearers" should read --wearer's--.

Column 13, Line 17, "el astomeric" should read --elastomeric--.

Column 16, Lines 12 & 13, "addi-tional" should read --addi-tionally--.

Column 16, Line 17, "patent application" should read --Patent Application--.

Column 16, Line 21, "patent application" should read --Patent Application--.

Column 18, Line 52, "previous" should read --pervious--.

UNITED STATES PATENT AND TRADEMARK OFFICE
CERTIFICATE OF CORRECTION

PATENT NO. : 5,368,584

DATED : November 29, 1994

INVENTOR(S) : Sandra H. Clear, et al.

It is certified that error appears in the above-identified patent and that said Letters Patent is hereby corrected as shown below:

Column 19, Line 35, "previous" should read --pervious--.

Column 20, Line 36, "previous" should read --pervious--.

Column 22, Line 5, "said said elastic side panel" should read --said elastic panel--.

Column 22, Line 10, "articleof" should read --article of--.

Signed and Sealed this

First Day of July, 1997

*Attest:*

BRUCE LEHMAN

*Attesting Officer*     *Commissioner of Patents and Trademarks*